US009554874B2

(12) United States Patent
Hegland

(10) Patent No.: US 9,554,874 B2
(45) Date of Patent: Jan. 31, 2017

(54) DENTAL DEVICES AND METHODS FOR TREATING ONE OR MORE TEETH

(71) Applicant: Hegland LLC, Clearwater, MN (US)

(72) Inventor: Lindsay Hegland, Clearwater, MN (US)

(73) Assignee: Hegland LLC, Plymouth, MN (US)

(*) Notice: Subject to any disclaimer, the term of this patent is extended or adjusted under 35 U.S.C. 154(b) by 221 days.

(21) Appl. No.: 14/194,203

(22) Filed: Feb. 28, 2014

(65) Prior Publication Data

US 2015/0245886 A1 Sep. 3, 2015

(51) Int. Cl.

| | |
|---|---|
| ***A61C 13/00*** | (2006.01) |
| ***A61C 5/10*** | (2006.01) |
| ***A61C 13/107*** | (2006.01) |
| *A61C 9/00* | (2006.01) |

(52) U.S. Cl.
CPC ............ *A61C 5/10* (2013.01); *A61C 13/0001* (2013.01); *A61C 13/0004* (2013.01); *A61C 13/0019* (2013.01); *A61C 9/0053* (2013.01)

(58) Field of Classification Search
CPC ......... A61C 5/08; A61C 5/10; A61C 13/0004; A61C 7/002
See application file for complete search history.

(56) References Cited

U.S. PATENT DOCUMENTS

| | | | | |
|---|---|---|---|---|
| 3,127,677 A * | 4/1964 | Schachter | ................ | A61C 7/12 433/17 |
| 4,611,288 A * | 9/1986 | Duret | ...................... | A61C 5/10 356/605 |
| 7,029,279 B2 * | 4/2006 | Schomann | ......... | A61C 13/0004 433/203.1 |
| 7,112,065 B2 * | 9/2006 | Kopelman | ......... | A61C 13/0004 433/213 |
| 7,442,041 B2 | 10/2008 | Imgrund | | |
| 7,458,812 B2 | 12/2008 | Sporbert | | |
| 7,474,932 B2 * | 1/2009 | Geng | ................ | A61C 13/0004 433/167 |
| 7,735,542 B2 | 6/2010 | Marshall | | |
| D690,423 S | 9/2013 | Pieroni | | |
| 8,562,339 B2 | 10/2013 | Raby | | |
| 9,339,351 B2 * | 5/2016 | Durandis | ................ | A61C 7/00 |
| 2009/0148813 A1 | 6/2009 | Sun | | |
| 2014/0011162 A1 | 1/2014 | Zegarelli | | |
| 2015/0182301 A1 | 7/2015 | Hegland | | |

OTHER PUBLICATIONS

Quercus Corporation, "Temporary Crown Restorations," 2nd edition, 64 pages, copyright 1979, updated 1991, revised Jun. 2005.

* cited by examiner

*Primary Examiner* — Ralph Lewis
(74) *Attorney, Agent, or Firm* — Fish & Richardson P.C.

(57) ABSTRACT

A dental device (such as a temporary dental crown or dental space maintainer), which may be fabricated in an intra-office process while the patient is located onsite, for use in securing to one or more teeth during a dental restoration procedure or another dental procedure.

20 Claims, 8 Drawing Sheets

600
614
604
618
602
613
607
616
608
612
620
610

500
502
504
506
508
510
512
514
516
518
520

DENTAL DEVICES AND METHODS FOR TREATING ONE OR MORE TEETH

TECHNICAL FIELD

The subject matter of this disclosure is related to dental devices and related methods of treating one or more teeth.

BACKGROUND

Dental caries afflicts people world-wide. In some cases, dental caries can be repaired through a process that involves removing decayed portions of a tooth and replacing the removed portions with a filling. Some cases of severe dental caries require the application of a dental crown. A dental crown can also be used to restore a tooth that has suffered a significant fracture, or has undermined dentinal support. In a typical crowning process, an impression of targeted tooth to be treated, surrounding teeth, and an opposing arch are taken. A dentist will then use a local anesthetic to numb the area around the targeted tooth. The dentist can then use a drill or laser to remove decayed portions of the tooth and perhaps other portions of the tooth. The dentist can then prepare the remaining portions of the tooth by isolating the tooth of bacteria, blood and/or debris. The dentist can then take an impression of the prepared tooth. A crown is created using impression models, but the crown can sometimes take days or weeks to manufacture, usually at a location remote from the dentist's office. When the crown is fabricated and delivered to the dentist, it can be inserted over the prepared tooth during a subsequent office visit. For example, a bonding agent (e.g., dental cement) can be used to adhere the crown to the prepared tooth.

In some circumstances, the dentist can insert a temporary crown over the prepared tooth after the impressions have been taken to allow a patient to eat and bite in a relatively normal fashion and protect sensitive dentin between the time the impressions are taken and the permanent crown is available for insertion over the prepared tooth. Such temporary crowns may be prefabricated in generic shapes and sizes by a third party supplier, and then stored in inventory at the dentist's office.

SUMMARY

Some embodiments of a system or method for treating one or more targeted teeth can employ a customized temporary crown that is formed according to the specific contours of a patient's mouth and teeth. For example, the temporary crown can be manufactured (e.g., in a dentist's facility using a three-dimensional printer apparatus or the like, during a single office visit) after the targeted tooth of the patient in the dentist's facility is prepared to receive a crown. As such, in some circumstances, the temporary crown is not necessarily a prefabricated crown that is intended to be used with any of a variety of differently sized and shaped teeth of any of a variety of different patients, but instead the temporary crown may optionally be promptly fabricated according to the specific anatomical shape and size of a particular tooth of a particular patient while that patient is waiting in the dental chair. Also, in some embodiments, the customized temporary crown can comprise a flexible, biocompatible, polymer material having a number of characteristics that can add efficiencies to the dental procedures, reduce the likelihood of excessive pressure or trauma to gingival tissues (thus reducing the risk of recession), maintain proper spacing between teeth, prevent shifting of teeth within the mouth, and provide an improved bite for a patient outfitted with the temporary crown. In some cases, the amount of cement used to retain a crown to a prepared tooth can be reduced. Finally, some of the systems and methods described herein are not limited to temporary crown devices, but instead can be used to provide a tooth spacer (for maintaining proper spacing between teeth and prevent shifting of teeth when a tooth is missing) or other dental device that is customized to fit with one or more teeth of a particular patient's mouth.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
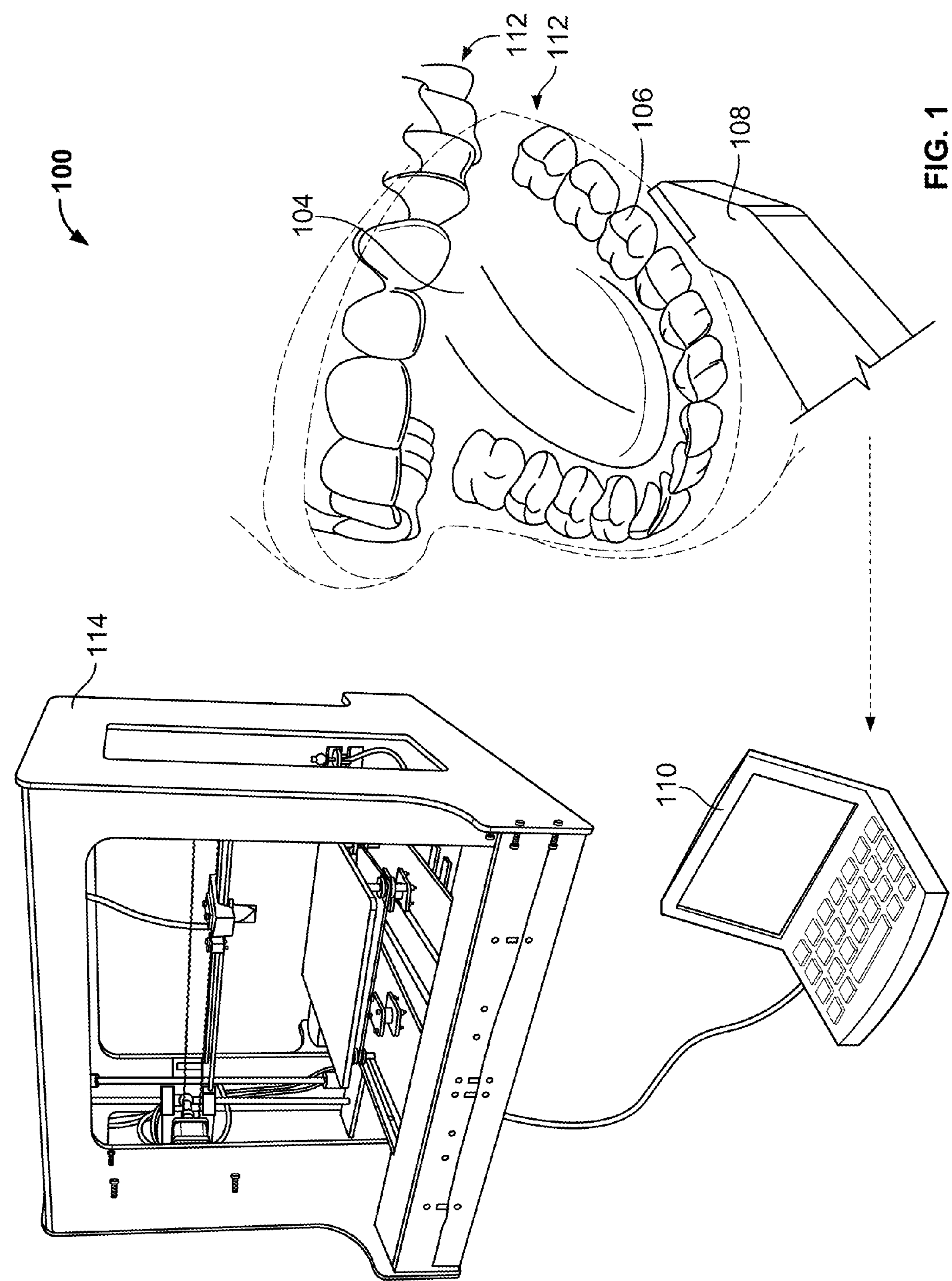
FIG. 1 shows a perspective view of a dental system, in accordance with some embodiments.
Figure 2:
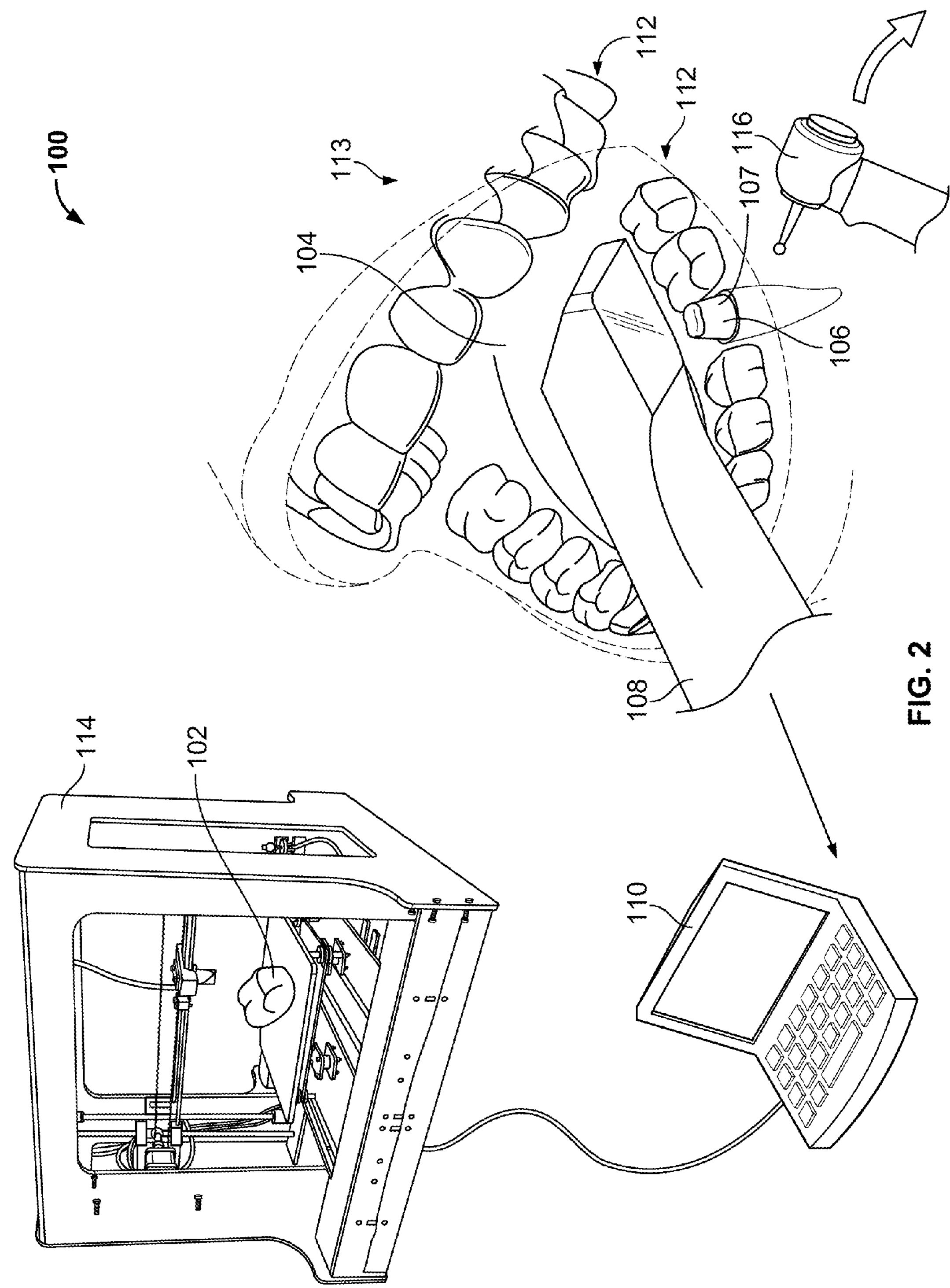
FIG. 2 shows a perspective view of the dental system of FIG. 1, including a customized temporary crown device.

Referring to FIGS. 1-2, some embodiments of a system 100 for treating one or more targeted teeth can employ a customized temporary crown 102 (FIG. 2) that can be formed to fit the specific contours of a particular targeted tooth 106 of a particular patient. As described in more detail below, the temporary crown 102 can be created onsite (e.g., at the same location in which the patient is located) and in response to the system 100 receiving digital images or another type of digital impression of one or more of the patient's teeth 112, including the targeted tooth 106 (e.g., in this embodiment, using a dental imaging wand 108 and a computer system 110). For example, the temporary crown 102 can be formed in an intra-office process (e.g., in a dentist's facility using a rapid fabrication machine 114 such as a three-dimensional printer apparatus or the like) using digital image information collected from scanning the targeted tooth 106 and nearby teeth 112 prior to preparation of the targeted tooth 106 (as shown in FIG. 1) as well as digital image information collected from scanning the targeted tooth 106 after it has been prepared to receive a crown (as shown in FIG. 1). In such embodiments, the temporary crown 102 is not necessarily a prefabricated article that is located in the inventory of the dentist's facility before the patient arrives, but instead the temporary crown 102 can be promptly fabricated according to the patient-specific anatomical shape and size of a particular tooth of a particular patient while that patient is waiting in the dental chair or in another area of the same dentist's facility. As described in more detail below, optionally, the customized temporary crown 102 can be implemented in a manner that adds efficiencies to the dental procedures (e.g., a temporary crown fitting procedure, a permanent crown fitting procedure, or another procedure), that improves embrasure forms between teeth, that reduces occlusal trauma, that reduces teeth drift, and that provides an improved fitting to the targeted tooth 106 so that a proper bite is maintained.

Referring to FIG. 1, in some implementations for creating the customized temporary crown 102, a practitioner such as a dentist can use a dental imaging wand 108 to perform an optical scan of the targeted tooth 106 and surrounding areas of a patient's mouth 104 prior to preparation of the targeted tooth 106 to obtain imaging data for generating a three-dimensional image of the targeted tooth 106 or another type of digital impression for the targeted tooth 106. For example, the dental scanning wand 108 can take digital images of the targeted tooth 106 and surrounding areas of the mouth 104, including adjacent teeth 112, which can be used as part of a process to create a three-dimensional Computer Aided Design (CAD) model of the customized temporary crown 102. The optical scan is performed prior to preparation of the targeted tooth 106 to accurately record the dimensions and surface features of the targeted tooth 106, as well as spacing between the targeted tooth 106 and other teeth 112 and portions of the mouth 104. In some implementations, the entire mouth 104 or the entire lower jaw of the patient is scanned. In some implementations, one or more teeth 112 of an arch opposing the targeted tooth 106 (such as one or more opposing teeth 113) are scanned. In some implementations, it is only necessary to scan the targeted tooth 106, the teeth 112 that are adjacent to the targeted tooth 106 and gingival areas near the targeted tooth 106. In some implementations, only the targeted tooth 106 is scanned using the dental imaging wand 108.

The dental imaging wand 108 can be connected to a computer system 110 so that the wand 108 is configured to transmit the captured imaging data to the computer system 110 for further processing. The dental imaging wand 108 transmits data indicative of the contours and shape of the targeted tooth 106 (and optionally, one or more neighboring teeth 112) to the computer system 110, which is configured to generate a three-dimensional digital image of the targeted tooth 106 or another type of digital impression of the targeted tooth 106. The dental scanning wand 108 can transmit information to the computer system 110 through wireless or wired communications. The computer system 110 can be, for example, a desktop or portable computer located in a dentist's office, a group of computers in communication with each other, or a remote computer in communication with a computing apparatus attached to the dental imaging wand 108 through a network. In some implementations, the computer system 110 can use digital imaging information captured by the dental imaging wand 108 to create a three-dimensional digital image of the targeted tooth 106 and areas of the mouth 104 in close proximity to the targeted tooth 106 (sometimes referred to as a digital dental impression).

It should be understood from the description herein that devices other than a dental imaging wand 108 can be used to capture imaging data of the targeted tooth 106 and surrounding portions of the mouth 104. For example, Magnetic Resonance Imaging (MRI) technology can be used to capture imaging data for use in generating the three-dimensional digital image of the targeted tooth 106. As another example, fluoroscope or x-ray images taken from several angles can serve as the imaging data used by the computer system 110 to generate the three-dimensional digital image of the targeted tooth 106. As yet another example, cone beam CT scan technology can be used to capture imaging data for use in generating the three-dimensional digital image of the targeted tooth 106.

Referring to FIG. 2, the dental procedure can include operations of identifying and removing decayed portions of the targeted tooth 106 so as to create a prepared tooth 107. In some implementations, the dental procedure can also or alternatively include removing portions of a fractured tooth. For example, a practitioner (e.g., a dentist or another clinician) can identify decayed portions of the targeted tooth 106 and remove the decayed portions using a dental drill 116 to prepare the tooth for application of a crown (e.g., a temporary crown, permanent crown, or both). In some implementations, one or more alternative dental tools can be used, rather than the dental drill 116, to remove decayed portions of the targeted tooth 106 when creating the prepared tooth 107. For example, a laser can be used to remove decayed portions of the targeted tooth 106. In some implementations, healthy portions of the targeted tooth 106 are removed in addition to decayed portions of the targeted tooth 106. Healthy portions of the targeted tooth 106 can be removed to create a proper shape for the prepared tooth 107 to better facilitate a proper fit between the prepared tooth 107 and a crown applied to the prepared tooth 107. In some implementations, as illustrated in FIG. 2, a slightly tapered shape for the prepared tooth 107, with the bottom being wider than the top, can facilitate easier application of a crown to the prepared tooth 107 than other possible shapes for the prepared tooth 107. For example, the preparation procedure can include approximately 0.5 mm to 2 mm of occlusal reduction and approximately 1 mm of axial reduction. As another example, the prepared tooth 107 can be prepared such that a 6 to 8 degree taper between the lower (cervical) portion of the tooth and upper (occlusal) portion of the tooth. In some implementations, portions of the targeted tooth 106's enamel and dentin are removed during the preparation phase. In some implementations, portions of restorative material (such as amalgam or resin) are removed during the preparation phase.

Still referring to FIG. 2, in some implementations for creating the customized temporary crown 102, a practitioner such as a dentist can obtain a digital dental impression of the prepared tooth 107 by using the dental imaging wand 108 to scan the prepared tooth 107 and, in some implementations, surrounding areas of the patient's mouth 104 after portions of the targeted tooth 106 have been removed to create the prepared tooth 107. For example, the dental scanning wand 108 can take digital images of the prepared tooth 107 and surrounding areas of the mouth 104, including adjacent teeth 112, which can be used as part of the process to create a three-dimensional Computer Aided Design (CAD) model of the customized temporary crown 102. In some implementations, the entire mouth 104 or the entire lower jaw of the patient is scanned. In some implementations, it is only necessary to scan the prepared tooth 107, the teeth 112 that are adjacent to the prepared tooth 107 and gingival areas near the prepared tooth 107. In some implementations, only the prepared tooth 107 is scanned using the dental imaging wand 108.

As described above, the dental imaging wand 108 can be connected to the computer system 110 so that the wand 108 is configured to transmit the captured imaging data to the computer system 110 for further processing. In some implementations, the computer system 110 can use digital imaging information captured by the dental imaging wand 108 to create a three-dimensional digital image of the prepared tooth 107 and areas of the mouth 104 in close proximity to prepared tooth 107 (sometimes referred to as a digital dental impression). Software running on the computer system 110 can then use the digital dental impression data collected for the targeted tooth 106 (FIG. 1) and the digital dental impression data collected for the prepared tooth 107 (FIG. 2) to generate a CAD model for fabricating the customized temporary crown 102.

In this embodiment, the computer system 110 receives the digital imaging information from the dental imaging wand 108 and executes a program to generate a CAD model for the customized temporary crown 102. For example, the computer system 110 can include a user interface (e.g., touchscreen, display, keyboard, mouse, etc.), computer-readable memory for storing the digital imaging information, and one or more processors that are configured to execute a software program stored in the computer-readable memory specifically configured to generate the CAD model for the customized temporary crown 102. In some implementations, the computer system 110 first generates a three-dimensional digital image of the targeted tooth 106 (prior to preparation) and a three-dimensional digital image of the prepared tooth 107 and then uses the generated three-dimensional digital images to generate the CAD model. In some implementations, the computer system 110 generates the CAD model without first creating a three-dimensional digital image of the targeted tooth 106 or prepared tooth 107. The computer system 110 generates the CAD model to define the customized temporary crown 102 to have patient specific, custom-shaped surfaces based on the contours of the targeted tooth 106, prepared tooth 107 and, in some cases, surrounding areas of the mouth 104, such as one or more of the teeth 112. The computer system 110 can include a desktop or portable computer or a custom computer system that is configured to interact with the dental scanning wand 108 and the three-dimensional printer 114.

The computer system 110 can generate the CAD model such that outer surfaces of the customized temporary crown 102 defined by the CAD model match the shape of outer surfaces of the targeted tooth 106 prior to preparation of the targeted tooth 106 and such that inner surfaces of the customized temporary crown 102 defined by the CAD model correspond to surfaces of the prepared tooth 107 created from removing portions of the targeted tooth 106. For example, the CAD model defines a shape for the inner surfaces of the customized temporary crown 102 such that the interior surfaces of the customized temporary crown 102 conform to the contours of prepared tooth 107 when the customized temporary crown 102 affixed to the prepared tooth 107. In some implementations, the digital dental impression data captured for the targeted tooth 106 is used to generate portions of the CAD model defining exterior surfaces of the customized temporary crown 102 while the digital dental impression data captured for the prepared tooth 107 is used to generate portions of the CAD model defining inner surfaces of the customized temporary crown 102. In some implementations, the computer system 110 can generate the CAD model such that outer surfaces of the customized temporary crown 102 defined by the CAD model enhance contours of the outer surfaces of the targeted tooth 106 prior to preparation of the targeted tooth 106 to create a better "bite" for the patient or to create preferred spacing among the teeth 112.

Generating the CAD model such that the customized temporary crown 102 created using the CAD model has outer surfaces matching the shape of outer surfaces of the targeted tooth 106 prior to preparation of the targeted tooth 106 can help to ensure that, once the customized temporary crown 102 is in place, proper spacing between the customized temporary crown 102 and adjacent teeth 112 is maintained and that a proper bite between the customized temporary crown 102 and opposing teeth 112 (such as opposing teeth 113) is maintained. This customized shape for the outer surfaces of the customized temporary crown 102 can prevent the patient from feeling discomfort when chewing or biting. The customized shape can also reduce the potential risk for pulpitis in the targeted tooth 106. Additionally, the customized shape of the customized temporary crown 102 can help to prevent shifting of the teeth 112 due to improper spacing between the customized temporary crown 102 (when in place over the prepared tooth 107) and adjacent teeth 112. The customized shape of the customized temporary crown 102 can also provide proper gingival margin contours which can reduce gingival inflammation. The customized shape of the internal surfaces of the customized temporary crown 102 can also reduce the amount of bonding agent (e.g., dental cement) needed to secure the customized temporary crown 102 to the prepared tooth 107, which can also facilitate easy removal of the temporary crown 102 (during a procedure in which a permanent crown is affixed).

In some implementations, dental impression data for one or more opposing teeth 113 is used in generating the CAD model of the customized temporary crown 102 to ensure that the customized temporary crown 102 generated using the CAD model provides a proper bite for the patient (when one or more of the opposing teeth 113 are in contact with the customized temporary crown 102). Maintaining proper centric contacts among the teeth 112 can help reduce potential excursive interference when a permanent crown is inserted. Additionally, maintaining proper spacing and prevention of teeth drift can reduce the need for adjustment of a subsequently inserted permanent crown to conform to a changed special relationship among the teeth 112. Additionally, by creating the customized temporary crown 102 as a crown having a shape customized to the patient, the need for adjustments to the size and/or shape of the customized temporary crown 102 after it is inserted over the prepared tooth 107 is reduced or eliminated.

Furthermore, generating the CAD model such that the customized temporary crown 102 created using the CAD model has inner surfaces corresponding to the shape of outer surfaces of the prepared tooth 107 can help ensure a proper fit between the customized temporary crown 102 and the prepared tooth 107 when the customized temporary crown 102 is affixed to the prepared tooth 107 within the patient's mouth 104. For example, the customized temporary crown 102 can be fabricated such that contours of the inside of the customized temporary crown 102 correspond to contours of the prepared tooth 107 to ensure a custom fit between the customized temporary crown 102 and the prepared tooth 107. Such a custom fit for the customized temporary crown 102 can reduce the need for adjustment of the customized temporary crown 102 by a dentist or other practitioner when the customized temporary crown 102 is adhered to the prepared tooth 107. Additionally, the custom fit for the customized temporary crown 102 can prevent slippage between the customized temporary crown 102 and the prepared tooth 107 when the customized temporary crown 102 is in use by the patient, such as when chewing, thus helping to prevent pre-mature loss or dislodgment of the temporary crown 102.

In some implementations, the CAD model defines portions of the outer surfaces of the customized temporary crown 102 to engage teeth and gums in close proximity to the prepared tooth 107 in a patient-specific, customized manner. For example, the dental imaging wand 108 can capture digital images of at least a portion of one of the neighboring teeth 112 positioned next to the prepared tooth 107 (or both of the neighboring teeth 112). The computer system 110 can use the digital information captured by the dental scanning wand 108 to generate the CAD model such that a portion of the outer surface of the customized temporary crown 102 is custom shaped to conform to the contours of a proximal surface of one of the adjacent teeth 112 that faces the prepared tooth 107. Such contour shaping of the outer surface of the customized temporary crown 102 can be used to define preferred embrasure forms between the customized temporary crown 102 (when in place in the mouth 104 over the prepared tooth 107) and adjacent teeth 112.

Referring to FIGS. 1-2, in some embodiments of the system 100, the computer system 110 can be in electronic communication with rapid fabrication machine 114 such as a three-dimensional printer. Examples of three-dimensional printers include FDM printers, SLA printers, and polyjet printers. For example, in the depicted embodiment, the computer system 110 can use the generated CAD model of the customized temporary crown 102 to transmit instructions to the three-dimensional printer 114 for fabricating the customized temporary crown 102. The three-dimensional printer 114 can produce the customized temporary crown 102 in an additive manner. For example, the three-dimensional printer 114 creates the customized temporary crown 102 by depositing and/or solidifying layers of material until a three-dimensional structure defined by the CAD model is complete. In some implementations, the three-dimensional printer 114 is located locally in the dentist's facility (e.g., within the walls of the dentist's facility while the patient is waiting within the same dentist's facility). When the three-dimensional printer 114 is located locally in the dentist's facility, the system 100 can be used to create a digital impression of the patient's mouth 104, fabricate the customized temporary crown 102, and apply the customized temporary crown 102 to the prepared tooth 107 all in one office visit.

The computer system 110 can use the generated CAD model of the customized temporary crown 102 to transmit instructions to the three-dimensional printer 114 to allow the three-dimensional printer 114 to create the patient-specific, customized temporary crown 102. For example, the computer system 110 can create an STL file using the generated CAD model and transmit the STL file to the three-dimensional printer 114. In some implementations, the computer system 110 creates digital cross-sections of the CAD model and transmits the digital cross-sections to the three-dimensional printer 114. The three-dimensional printer 114 uses the digital cross-sections as guides for "printing" successive layers of the customized temporary crown 102. In some implementations, the computer system 110 transmits a file that includes the CAD model to the three-dimensional printer 114 and the digital cross-sectioning of the CAD model is performed by the three-dimensional printer 114.

The three-dimensional printer 114 can be configured to fabricate the temporary crown 102 so that the resulting product comprises a semi-rigid yet flexible, biocompatible, polymer material. Fabricating the customized temporary crown 102 from a flexible material can produce an improved bite for the patient by reducing discomfort from contact between the customized temporary crown 102 (when inserted within the mouth 104 over the prepared tooth 107) and opposing teeth 113 when the patient is chewing or biting (reduction of occlusal trauma). In some implementations, the customized temporary crown 102 is fabricated using a white colored material to provide a pleasing aesthetic look for the customized temporary crown 102 when in place over the prepared tooth 107.

In some embodiments, the material used by the three-dimensional printer 114 to create the customized temporary crown 102 comprises a polymer material. Examples of three-dimensional printing materials that can be used by the three-dimensional printer 114 include acrylonitrile butadiene (ABS), polypropylene, high-density polyethylene, polystyrene, high impact polystyrene (HIPS), polylactic acid (PLA), Soft PLA, PLA 4043d, thermoplastic elastomer (TPE), bendlay, t-glase, poly methyl methacrylate, polycarbonates, acrylonitrile butadiene styrene, high-impact polystyrene, styrene-based thermoplastic elastomers, or ethylene propylenediene monomer rubber.

Figure 3:
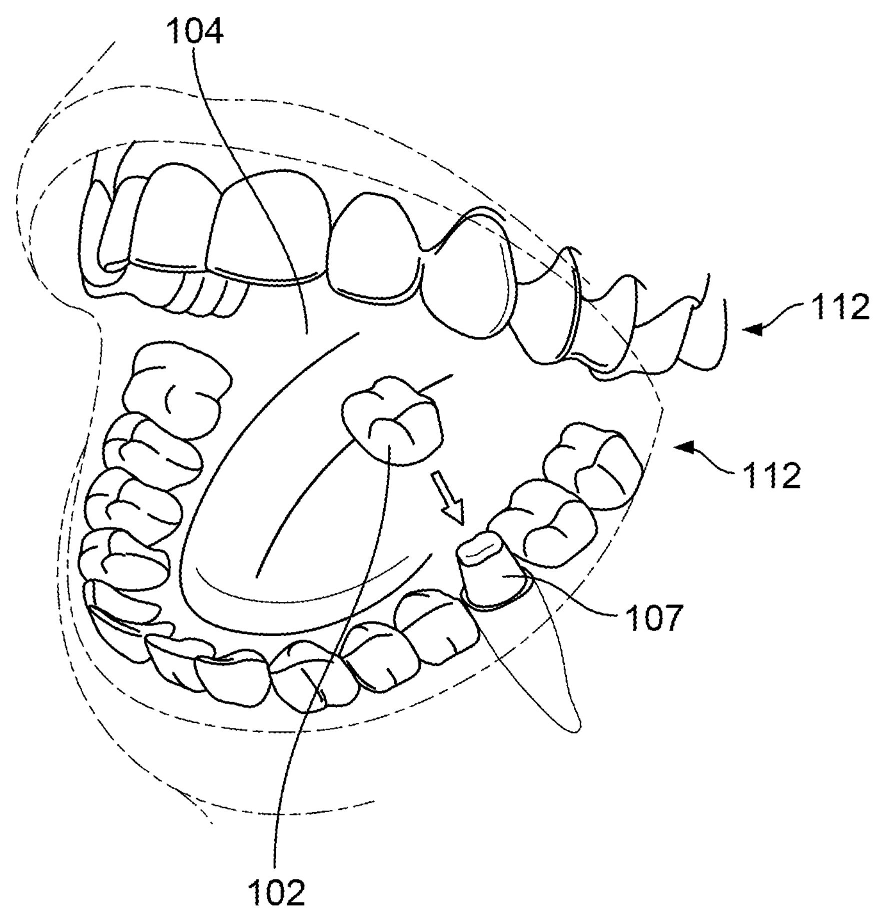
FIG. 3 shows a perspective view of the customized temporary crown of FIG. 2 being inserted over a prepared, targeted tooth, in accordance with some embodiments.

Referring to FIG. 3, after the customized temporary crown 102 has been created, the customized temporary crown 102 is inserted into the mouth 104 such that the customized temporary crown 102 intimately adapts to the prepared tooth 107 and engages the patient-specific contours of the prepared tooth 107 (including the cervical-third, or lower ⅓, of the tooth near the gingival tissue). In some implementations, a temporary cement (such as zinc oxide eugenol) is applied to the prepared tooth 107 prior to insertion of the customized temporary crown 102 to adhere inner surfaces of the customized temporary crown 102 to the prepared tooth 107. As described above, the customized shape for the inner surfaces of the customized temporary crown 102 creates a custom fit with the patient-specific contours of the prepared tooth 107 to reduce the need for adjustment of the customized temporary crown 102 during insertion, and to reduce the likelihood of the customized temporary crown 102 becoming dislodged from the prepared tooth 107 after insertion.

After insertion, the customized temporary crown 102 can be worn in the patient's mouth 104 for a period of weeks or months. For example, a typical duration for use of a temporary crown prior to insertion of a permanent crown can be 2 to 4 weeks. The customized temporary crown 102 can be worn in the patient's mouth 104 until a permanent crown is ready for insertion. When the permanent crown is ready, the patient can return to the practitioner's office (or the office of another practitioner) to have the customized temporary crown 102 replaced with the permanent crown. During the procedure, the customized temporary crown 102 can be removed from the prepared tooth 107. The permanent crown is then placed over the prepared tooth 107 and adhered to the prepared tooth 107 using a bonding fluid (e.g., dental cement). The customized shape of the temporary crown 102 (that corresponds to the shape of the targeted tooth 106 prior to preparation) can reduce the amount of time needed to perform the permanent crown insertion procedure since the customized shape of the temporary crown 102 can help maintain proper spacing among the teeth 112 and prevent drifting of the teeth 112. By ensuring that proper spacing is maintained, the customized temporary crown 102 reduces the need for adjustments to the shape of the permanent crown that might otherwise be necessary in response to shifting of the teeth 112.

Figure 4A:
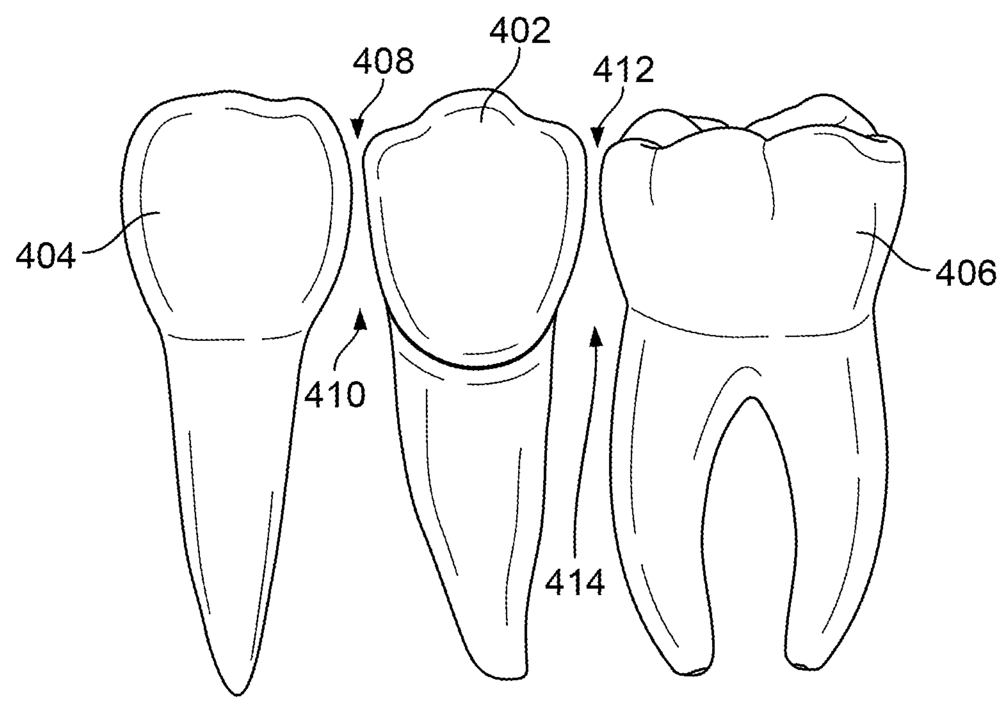
FIG. 4A shows a side view of a customized temporary crown inserted over a targeted tooth in relation to adjacent healthy teeth.
Figure 4B:
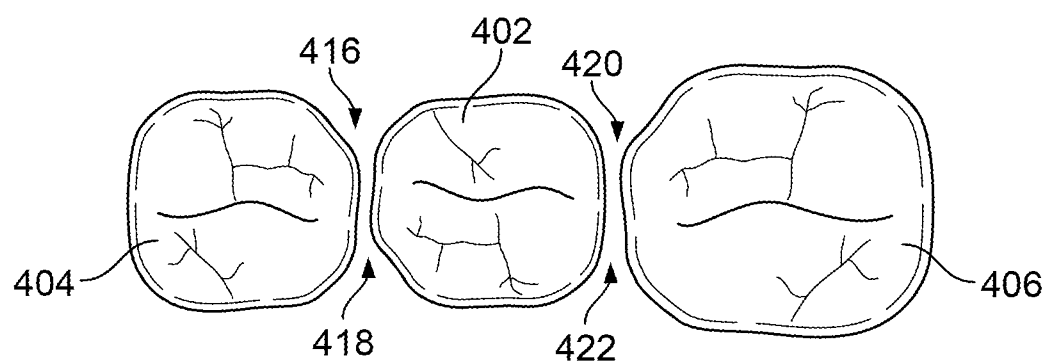
FIG. 4B shows a top view of the customized temporary crown and adjacent healthy teeth of FIG. 4A.

Referring now to FIGS. 4A-B, the system or processes described above can be implemented to provide a customized temporary crown 402 for insertion over a prepared tooth between healthy teeth 404 and 406 (or in some implementations, a combination of one or more healthy teeth and one or more other crowns). For example, the customized temporary crown 402 depicted in FIGS. 4A-B can be rapidly fabricated in an intra-office procedure in a manner similar to that of the temporary crown 102 described in connection with FIGS. 1-3. FIG. 4A shows a side or lingual view of the customized temporary crown 402 positioned between the teeth 404 and 406 located within a patient's mouth, while FIG. 4A shows the same positioning among the customized temporary crown 402 and the teeth 404 and 406 in a top down or occlusal view.

FIGS. 4A-B show the customized temporary crown 402 as maintaining proper relational spacing with respect to the teeth 404 and 406 after the customized temporary crown 402 has been inserted over a prepared tooth. The customized shape of exterior surfaces of the temporary crown 402 allows the temporary crown 402 to maintain the same spacing between the customized temporary crown 402 and the teeth 404 and 406 as was present between the teeth 404 and 406 and a decayed tooth that has been restored using the customized temporary crown 402. Referring to FIG. 4A, the proper relational spacing achieved between the customized temporary crown 402 and the teeth 404 and 406 includes an occlusal embrasure 408 and a cervical (or gingival) embrasure 410 between the customized temporary crown 402 and the tooth 404, and an occlusal embrasure 412 and a cervical (or gingival) embrasure 414 between the customized temporary crown 402 and the tooth 406. It should be understood from the description herein that the occlusal embrasures 408, 412 and the cervical embrasures 410, 414 are not necessarily depicted in a perfect scale in FIG. 4A, but instead may be slightly enlarged in this view for purposes of illustration only.

The aforementioned system 100 can be employed to restore a decayed tooth and maintain proper occlusal and cervical embrasure at the end of a temporary crown creation and insertion procedure by providing the customized temporary crown 402. For example, the system 100 (FIG. 1) can be used to fabricate the customized temporary crown 402 (FIGS. 4A-B) that defines the selected occlusal embrasures 408 and 412 and the selected cervical embrasures 410 and 414 for purposes of hindering food from becoming lodged between the teeth 404 and 406 and the customized temporary crown 402, and to stabilize a dental arch of the patient by assuring consistent anchorage of teeth within the patient's mouth. Also, the temporary crown 402 can define the selected occlusal embrasures 408 and 412 and the selected cervical embrasures 410 and 114 to preserving proper contact points between the teeth 404 and 406 and the customized temporary crown 402 for purposes of reducing the likelihood of "drifting" of teeth within the patient's mouth. Additionally, the customized temporary crown 402 can provide a comfortable, customized bite between the customized temporary crown 402 and opposing teeth. Additionally, maintaining proper embrasures can facilitate proper gingiva health.

Similarly, as shown in FIG. 4B, the system 100 can be used to fabricate the customized temporary crown 402 to define a selected buccal embrasure 416 and a selected lingual embrasure 418 between the customized temporary crown 402 and the tooth 404. Additionally, the customized temporary crown 402 can define a selected buccal embrasure 420 and a selected lingual embrasure 422 between the customized temporary crown 402 and the tooth 406. It should be understood from the description herein that the buccal embrasures 416, 420 and the lingual embrasures 418, 422 are not necessarily depicted in a perfect scale in FIG. 4B, but instead may be slightly enlarged in this view for purposes of illustration only. Having proper buccal and lingual embrasures between the teeth 404 and 406 and the customized temporary crown 402 can also hinder food from becoming lodged between the teeth 404 and 406 and the customized temporary crown 402. In some implementations, the buccal and lingual embrasures as defined by the temporary crown 402 provide an adequate breadth of the proximal contacts between the customized temporary crown 402 and the teeth 404 and 406 to minimize lodging of food between the teeth 404 and 406 and the customized temporary crown 402. Accordingly, the temporary crown 402 can be tailored to each patient's specific anatomical features of a targeted tooth being restored and neighboring teeth, and furthermore, the temporary crown 102 can be promptly fabricated (while the patient is waiting in the dental facility) according to the specific anatomical shapes and sizes of that particular patient's mouth.

Figure 5:
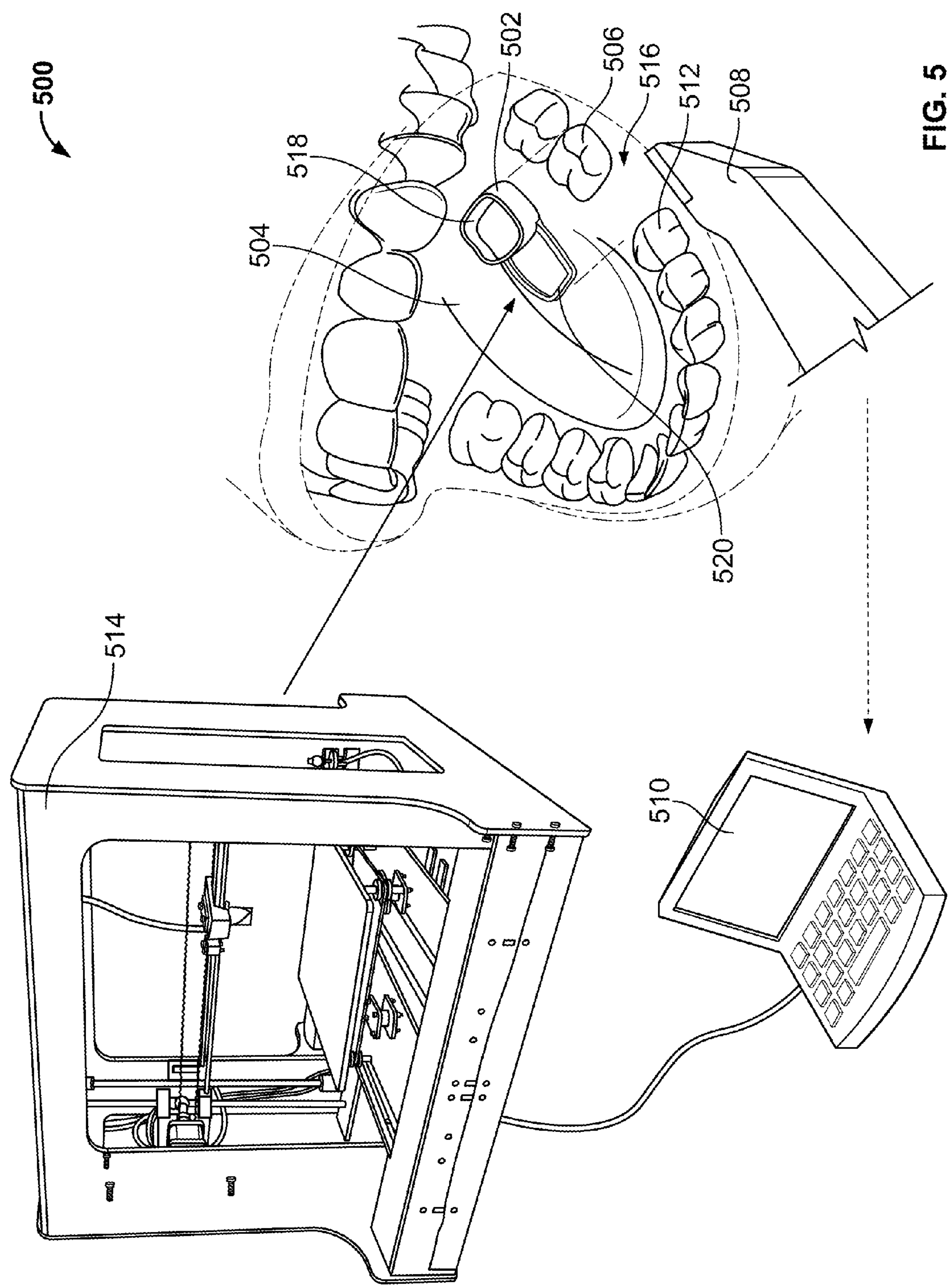
FIG. 5 shows a perspective view of a dental system, including a customized unilateral space maintainer.

Referring to FIG. 5, some embodiments of a system 500 for maintaining proper dental spacing can employ a customized unilateral space maintainer 502 to fit the patient-specific contours of one or more teeth within a patient's mouth 504. For example, the customized unilateral space maintainer 502 can be fabricated to form a custom fit with a tooth 506 and to maintain proper spacing between the tooth 506 and a tooth 512. In some implementations, a space 516 between the teeth 506 and 512 can arise due to the loss or absence of a tooth. For example, a child can lose a "baby tooth" before an "adult tooth" is ready to erupt. The customized unilateral space maintainer 502 can maintain the proper spacing of the space 516, reducing the likelihood of drifting of remaining teeth within the mouth 504 prior to eruption of the "adult tooth" within the vacant space 516. The customized unilateral space maintainer can help prevent ectopic eruption or impaction of a delayed permanent tooth when the tooth erupts from a space 516. In other implementations, the customized unilateral space maintainer 502 can be used to maintain a space where an adult (or permanent) tooth has been removed or become dislodged, thereby reducing the likelihood of drifting of remaining teeth within the mouth 504. The space can then be properly restored in a future procedure, such as a tooth implantation procedure, or a bridge procedure.

The customized unilateral space maintainer 502 can include a securing portion 518 for engaging and securing to the tooth 506 and a space maintaining portion 520 that, when the unilateral space maintainer 502 is positioned within the patient's mouth 504, maintains a proper spacing for the space 516 between the teeth 506 and 512. The customized unilateral space maintainer 502 can prevent tooth "drift" within the mouth 504 by maintaining the space 516 and defining a proper distance between the tooth 506 and the tooth 512 in the absence of a tooth in the space 516.

In some implementations, the unilateral space maintainer 502 can be created onsite (e.g., at the same location in which the patient located) and in response to the system 500 receiving digital images or another type of digital impression of portions of the patient's mouth 504, including the teeth 506 and 516 (e.g., using a dental imaging wand 508 and a computer system 510). For example, the unilateral space maintainer 502 can be formed in an intra-office process (e.g., in a dentist's facility using a rapid fabrication machine 514 such as a three-dimensional printer apparatus or the like) for use in maintaining a proper distance between the teeth 506 and 512 across the space 516. In such embodiments, the unilateral space maintainer 502 is not necessarily a prefabricated, generically sized article that is located in the inventory of the dentist's facility before the patient arrives, but instead the unilateral space maintainer 502 can be promptly fabricated according to the specific anatomical shape and size of the patient's mouth 504, including the teeth 506 and 512, while that patient is waiting in the dental chair or in another area of the same dentist's facility. The customized unilateral space maintainer 502 can be implemented in a manner that adds efficiencies to the dental procedures, such as reduction of time required to adjust the unilateral space maintainer when inserted into the mouth 504. Additionally, if the customized unilateral space maintainer 502 is being used to maintain a space where a tooth had been removed by a practitioner, the customized unilateral space maintainer 502 can be fabricated and inserted in the same office visit during which the tooth was removed. In some implementations, the customized unilateral space maintainer 502 is fabricated to conform to patient specific contours of the tooth 506 and the patient specific length and/or width of the space 516.

Briefly, in use, the customized unilateral space maintainer 502 can be inserted into a mouth 504 of a patient such that the securing portion 518 surrounds the tooth 506 and engages surfaces of the tooth 506 in a customized fit specific to that particular tooth 506. For example, imaging data collected for the tooth 506 is used to generate patient specific contours for the inner surfaces of the securing portion 518 that conform to contours of the tooth 506 (including the cervical-third, or lower ⅓, of the tooth 506 near the gingival tissue). Due to the customized fit of the unilateral space maintainer 502, it can form a seal with a lower cervical rim of the targeted tooth 106 to thereby reduce patient discomfort and the likelihood of the customized unilateral space maintainer 502 becoming unintentionally dislodged from the patient's mouth 504. In some implementations, the customized unilateral space maintainer 502 is fabricated such that the securing portion 518 comprises a flexible polymer material that allows the securing portion 518 to be readily inserted around the tooth 506. Because the securing portion 518 can be formed of a flexible polymer material, the material at the lower opening may elastically flex during an insertion procedure while passing over the upper occlusal portion of the tooth 506 before seating at the lower cervical portion of the tooth 506 in a snug fit.

In the depicted embodiments, the customized unilateral space maintainer 502 is preferably inserted into the mouth 504 such that the securing portion 518 fully surrounds the tooth 506, leaving a top surface of the tooth 506 exposed. In some implementations, a bonding agent is used to adhere the customized unilateral space maintainer 502 to the tooth 506. Additionally, the customized unilateral space maintainer 502 is preferably inserted into the mouth 504 such that the space maintaining portion 520 extends away from the tooth 506, across the space 516, and contacts a surface of the tooth 512 facing the tooth 506 at a proper proximal contact. The customized unilateral space maintainer 502 can be fabricated such that the length of the space maintaining portion 520 corresponds to the patient specific length of the space 516 to maintain proper spacing of teeth within the mouth 504.

The customized unilateral space maintainer 502 can be fabricated using a process similar to those described above for fabricating customized temporary dental crowns. For example, a process for fabricating the customized unilateral space maintainer 502 can closely resemble the process described above in connection with FIGS. 1-2 for fabricating the customized temporary crown 102 (FIG. 2). In some implementations, a process for fabricating the customized unilateral space maintainer 502 can include acquiring digital imaging data for the teeth 506 and 512 and areas of the mouth 504 adjacent to and between the teeth 506 and 512 using the digital imaging wand 508. The digital imaging data can then be transferred to the computer system 510 for use in generating a three-dimensional model of the teeth 506 and 512 and portions of the mouth 504. The computer system 510 can be, for example, a personal computer, a specialized computer system, or a network of computers coupled with Computer Aided Design (CAD) software for generating three-dimensional models. The computer system 510 can use a generated three-dimensional model of the teeth 506 and 512 and portions of the mouth 504 to generate a three-dimensional model (e.g., a CAD model) of the customized unilateral space maintainer 502.

The computer system 510 can then transfer data indicative of the three-dimensional model of the customized unilateral space maintainer 502 to the rapid fabrication machine 514 (e.g., a three-dimensional printer). In some implementations, information provided to the rapid fabrication machine 514 can include digital cross-sections of the CAD model created by the computer system 510. The rapid fabrication machine 514 uses the digital cross-sections as guides for "printing" successive layers of the customized unilateral space maintainer 502. In some implementations, the computer system 510 transmits a file that includes the CAD model to the rapid fabrication machine 514 and the digital cross-sectioning of the CAD model is performed by the rapid fabrication machine 514.

In some implementations, digital impression data for the teeth 506 and 512 and portions of the mouth 504 are acquired and the customized unilateral space maintainer 502 is fabricated on-site in a practitioner's office during a single office visit. After the customized unilateral space maintainer 502 has been created, the customized unilateral space maintainer 502 can be inserted into the patient's mouth 504 to maintain a proper distance between the teeth 506 and 512. Although the space maintainer 502 is described as a unilateral space maintainer, other customized space maintainers (e.g., bilateral space maintainers, crown and loop space maintainers, or other types) can be fabricated and inserted into a patient's mouth using similar processes to those described above.

Figure 6:
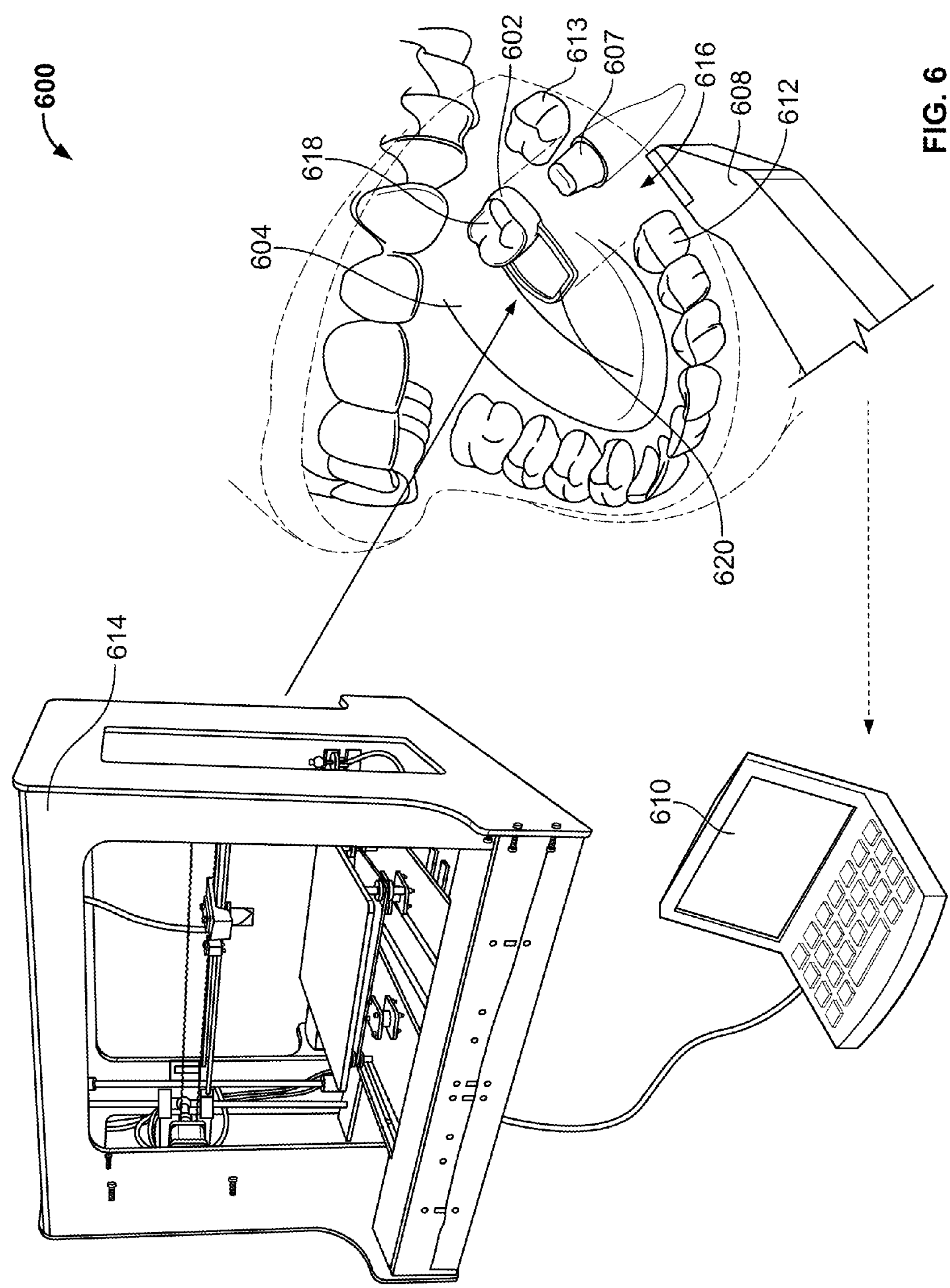
FIG. 6 shows a perspective view of a dental system, including a customized crown and loop space maintainer.

For example, referring to FIG. 6, similar processes can be used in accordance with some embodiments of a system 600 for maintaining proper dental spacing. For example, the system 600 can employ a customized crown and loop space maintainer 602 to fit the patient-specific contours of one or more teeth within a patient's mouth 604. For example, the customized crown and loop space maintainer 602 can be fabricated to form a custom fit with a prepared tooth 607 and to maintain proper spacing between the prepared tooth 607 and a tooth 612 (e.g., maintain a proper length for a space 616 between the tooth 612 and the prepared tooth 607). The customized crown and loop space maintainer 602 can prevent tooth "drift" within the mouth 604 by maintaining the space 616 and defining a proper distance between the prepared tooth 607 and the tooth 612 in the absence of a tooth in the space 616.

The customized crown and loop space maintainer 602 can include a crown portion 618 for engaging the prepared tooth 607 and a space maintaining portion 620 that, when the crown and loop space maintainer 602 is positioned within the patient's mouth 604, maintains a proper spacing for the space 616. The space maintaining portion 620 can be fabricated in a process similar to that described above in connection with FIGS. 1-2 for the customized temporary crown 102. For example, a dental imaging wand 608 can be used to collect a first set of digital imaging data prior to the prepared tooth 607 being prepared (i.e., prior to removal of tooth material from a decayed tooth). The dental imaging wand can then be used to collect a second set of digital imaging data of the prepared tooth 607 and surrounding areas of the mouth 604 after the prepared tooth 607 has been prepared to receive the customized crown and loop space maintainer 602.

In some implementations, the crown and loop space maintainer 602 can be created onsite (e.g., at the same location in which the patient located) and in response to the system 600 receiving digital images or another type of digital impression of portions of the patient's mouth 604, including the prepared tooth 607 prior to preparation, the prepared tooth 607 after preparation, and the tooth 612 (e.g., using a dental imaging wand 608 and a computer system 610). For example, the crown and loop space maintainer 602 can be formed in an intra-office process (e.g., in a dentist's facility using a rapid fabrication machine 614 such as a three-dimensional printer apparatus or the like) for use in maintaining a proper distance between the prepared tooth 607 and the tooth 612 across the space 616. In such embodiments, the crown and loop space maintainer 602 is not necessarily a prefabricated, generically sized article that is located in the inventory of the dentist's facility before the patient arrives, but instead the crown and loop space maintainer 602 can be promptly fabricated according to the specific anatomical shape and size of the patient's mouth 604, including the prepared tooth 607 and the length of the space 616, while that patient is waiting in the dental chair or in another area of the same dentist's facility. The customized crown and loop space maintainer 602 can be implemented in a manner that adds efficiencies to the dental procedures, such as reduction of time required to adjust the unilateral space maintainer when inserted into the mouth 604. In some implementations, the customized crown and loop space maintainer 602 is fabricated to conform to patient specific contours of the prepared tooth 607 and the patient specific length and/or width of the space 616.

Briefly, in use, the customized crown and loop space maintainer 602 can be inserted into a mouth 604 of a patient such that inner surfaces of the crown portion 618 engage contours of outer surfaces of the prepared tooth 607. For example, imaging data collected for the prepared tooth 607 is used to generate patient specific contours for the inner surfaces of the crown portion 618 that conform to contours of the prepared tooth 607. In some implementations, a bonding agent is used to adhere inner surfaces of the crown portion 618 to the prepared tooth 607. Additionally, the customized crown and loop space maintainer 602 can be fabricated such that outer surfaces of the crown portion 618 match surfaces of the tooth 607 prior to preparation of the prepared tooth 607. Matching patient-specific contours of the pre-preparation tooth 607 can help to maintain proper spacing between the customized crown and loop space maintainer 602 and an adjacent tooth 612 when the customized crown and loop space maintainer 602 is inserted in the mouth 604. Additionally, a customized shape for the crown portion 618 can help ensure that a proper bite between the crown portion 618 and opposing teeth exists after insertion of the customized crown and loop space maintainer 602 in the mouth 604.

The customized crown and loop space maintainer 602 is preferably inserted into the mouth 604 such that the space maintaining portion 620 extends away from the prepared tooth 607, across the space 616, and contacts a surface of the tooth 612 facing the prepared tooth 607. The customized crown and loop space maintainer 602 can be fabricated such that the length of the space maintaining portion 620 corresponds to the patient specific length of the space 616 to maintain proper spacing of teeth within the mouth 604.

The customized crown and loop space maintainer 602 can be fabricated using a process similar to those described above for fabricating customized temporary dental crowns. For example, a process for fabricating the customized crown and loop space maintainer 602 can closely resemble the processes described above in connection with FIGS. 1-2 for fabricating the customized temporary crown 102 (FIG. 2). In some implementations, a process for fabricating the customized crown and loop space maintainer 602 can include acquiring digital imaging data for the prepared tooth 607 (both before and after preparation of the prepared tooth 607), the tooth 612, and areas of the mouth 604 adjacent to and between the prepared tooth 607 and the tooth 612 using the digital imaging wand 608. The computer system 610 can use the collected digital imaging data to generate a three-dimensional model (e.g., a CAD model) of the customized crown and loop space maintainer 602.

The computer system 610 can then transfer data indicative of the three-dimensional model of the customized crown and loop space maintainer 602 to the rapid fabrication machine 614 (e.g., a three-dimensional printer). In some implementations, information provided to the rapid fabrication machine 614 can include digital cross-sections of the CAD model created by the computer system 610. The rapid fabrication machine 614 uses the digital cross-sections as guides for "printing" successive layers of the customized crown and loop space maintainer 602. In some implementations, the computer system 610 transmits a file that includes the CAD model to the rapid fabrication machine 614 and the digital cross-sectioning of the CAD model is performed by the rapid fabrication machine 614.

In some implementations, digital impression data for the prepared tooth 607, tooth 612, and portions of the mouth 604 are acquired and the customized crown and loop space maintainer 602 is fabricated on-site in a practitioner's office during a single office visit. After the customized crown and loop space maintainer 602 has been created, the customized crown and loop space maintainer 602 can be inserted into the patient's mouth 604 to maintain a proper distance between the prepared tooth 607 and the tooth 612.

Figure 7:
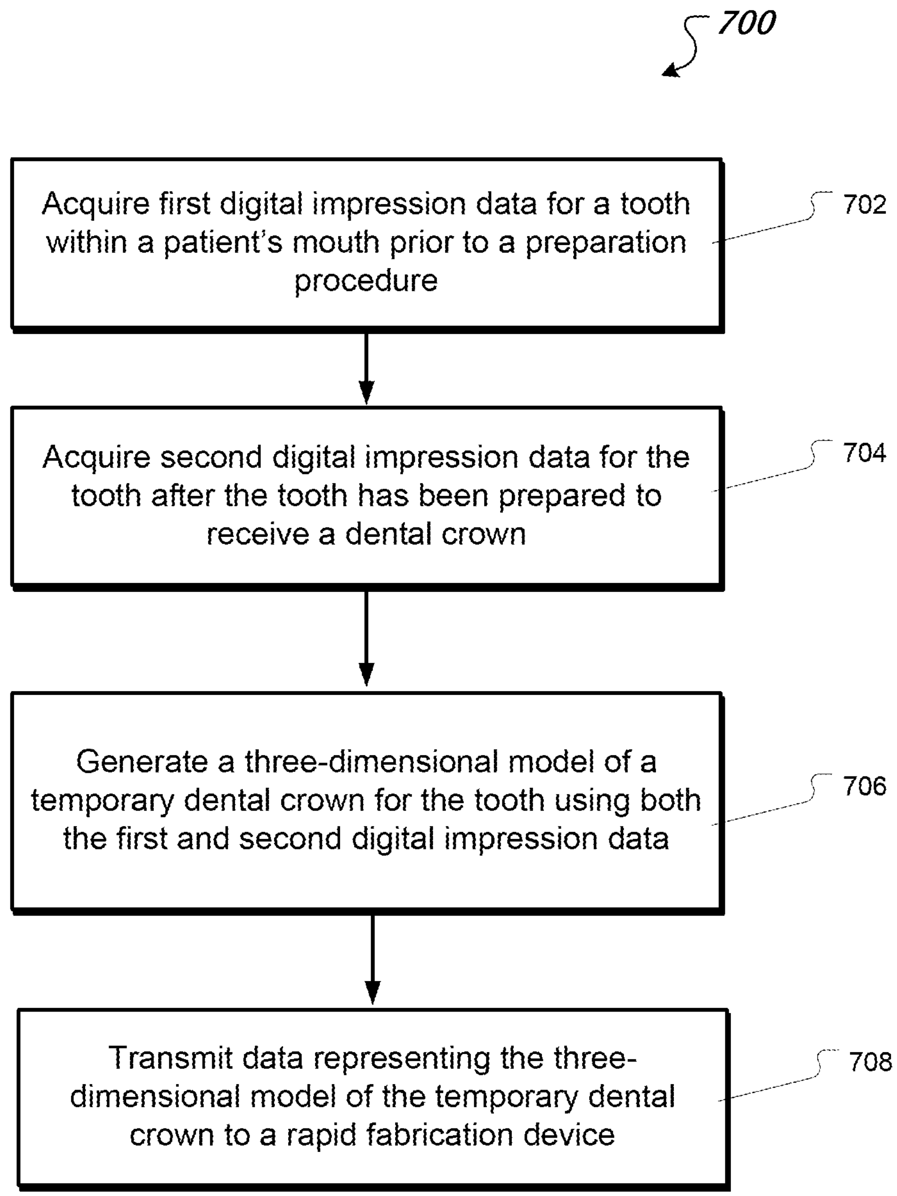
FIG. 7 is a flowchart illustrating an example procedure for creating and using a customized temporary crown during a dental procedure.

Referring now to FIG. 7, an example process 700 for making a customized temporary dental crown includes acquiring first digital impression data for a tooth within a patient's mouth prior to a preparation procedure (702). In some implementations, the first digital impression data can also include digital impression data for areas of the mouth near the tooth, or portions of the mouth opposite the tooth. For example, a practitioner, such as a dentist can use a dental scanning wand (e.g., the dental scanning wand 108 of FIGS. 1-2) to perform an optical scan and collect digital impression data for the tooth and other portions of the patient's mouth.

In some implementations, the dental scanning wand is used to collect digital impression data for a tooth identified for restoration through a dental crown application procedure. In some implementations, devices other than a dental scanning wand can be used to acquire the digital impression data. For example, Magnetic Resonance Imaging (MRI), cone beam CT, fluoroscope or x-ray technology can be used to acquire the digital impression data. In some implementations, the digital impression data is acquired from the dental scanning wand (or other imaging device) by a computer system such as the computer system 110 of FIGS. 1-2.

The process 700 further includes acquiring second digital impression data for the tooth after the tooth has been prepared to receive a dental crown (704). For example, a dentist or other practitioner can prepare the tooth to receive a dental crown by removing decayed portions of the tooth with a drill, laser, or other dental tool. In some implementations, the practitioner removes healthy portions of the tooth in addition to decayed portions of the tooth to create a proper shape for the tooth for receiving the dental crown. After the tooth has been prepared to receive the dental crown, the practitioner can use a dental scanning wand (e.g., the dental scanning wand 108 of FIGS. 1-2) to perform an optical scan and collect digital impression data for the prepared tooth and other portions of the patient's mouth. In some implementations, devices other than a dental scanning wand can be used to acquire the digital impression data. For example, Magnetic Resonance Imaging (MRI), cone beam CT, fluoroscope or x-ray technology can be used to acquire the digital impression data. In some implementations, the digital impression data is acquired from the dental scanning wand (or other imaging device) by a computer system such as the computer system 110 of FIGS. 1-2.

The process 700 further includes generating a three-dimensional model of a temporary crown for the tooth using both the first and second digital impression data (706). For example, the computer system can use the first and second digital impression data to generate a CAD model for fabricating a customized temporary dental crown. The first impression data of the pre-preparation tooth can be used to generate the CAD model such that the model defines contours of outer surfaces of the temporary dental crown to ensure proper spacing between the temporary dental crown and other teeth within the patient's mouth after the temporary dental crown is inserted into the patient's mouth. Generating a custom, patient-specific shape for the outer surfaces of the temporary dental crown, such that the outer surfaces of the temporary dental crown match outer surfaces of the tooth prior to preparation, can ensure that a proper bite between the temporary dental crown and opposing teeth is created once the temporary dental crown is inserted within the patient's mouth. The second impression data collected for the tooth after preparation can be used to define contours of inner surfaces of the temporary dental crown, so that the inner surfaces correspond to contours of the tooth after preparation to allow for a more secure and comfortable fit between the temporary dental crown and the tooth when the dental crown is inserted over the tooth.

The process 700 further includes transmitting data representing the three-dimensional model of the temporary dental crown to a rapid fabrication device (708). For example, the computer system can transmit data representing the three-dimensional model to a three-dimensional printer (e.g., the three-dimensional printer 114 of FIG. 1). The rapid fabrication device can use the transmitted data representing the three-dimensional model to create the temporary dental crown. After creation of the custom temporary dental crown, the temporary dental crown can be affixed to the prepared tooth within the patient's mouth.

In some implementations, digital cross-sections of the three-dimensional model are created and transmitted to the rapid fabrication device. For example, a three-dimensional printer can use the digital cross-sections as guides for depositing and/or solidifying successive layers of material to create the temporary dental crown. In some implementations, a file that includes entire three-dimensional model (such as a CAD file) is transmitted to the rapid fabrication device. In some such implementations, digital cross-sectioning of the three-dimensional model is performed by rapid fabrication device. In some implementations, digital cross-sections are not required by the rapid fabrication device to generate the temporary dental crown.

Figure 8:
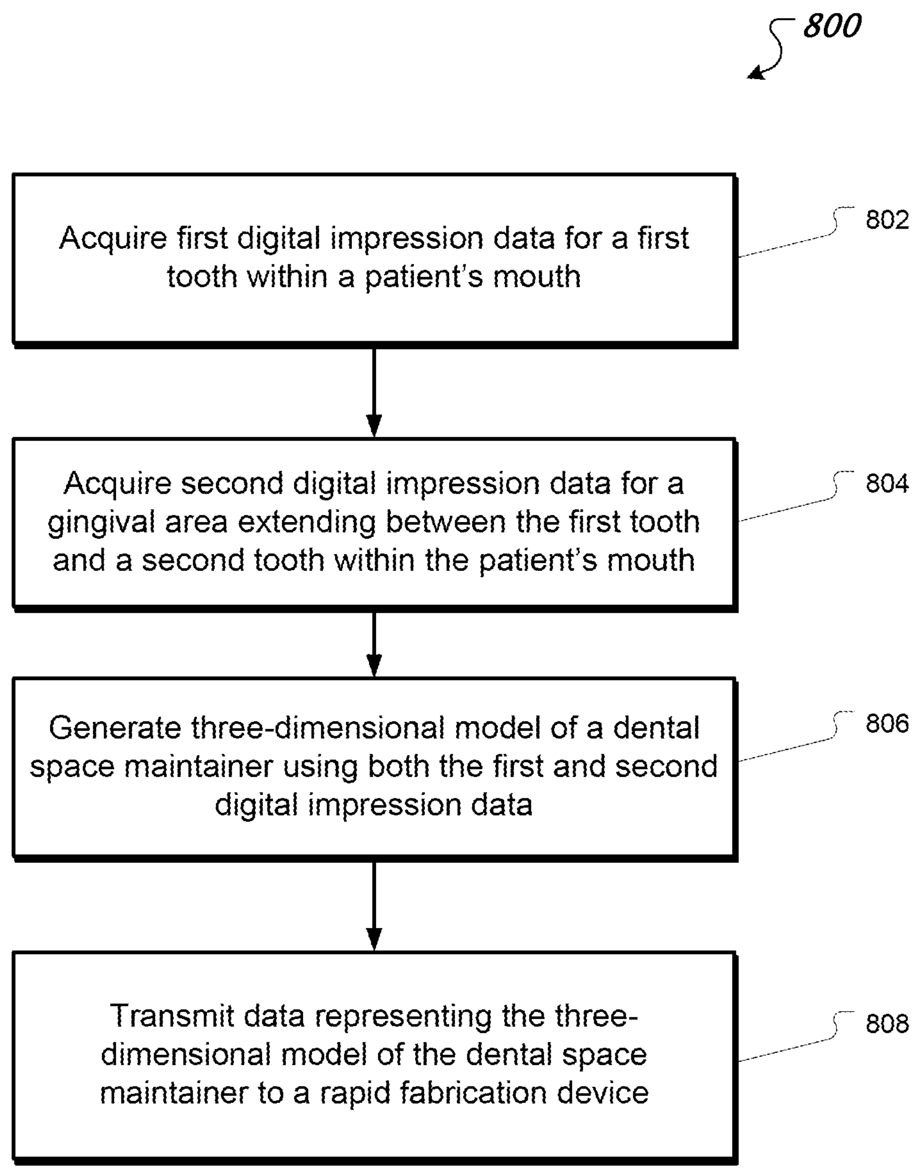
FIG. 8 is a flowchart illustrating an example procedure for creating and using a customized dental spacer during a dental procedure.

Referring now to FIG. 8, an example process 800 for making a customized dental space maintainer includes acquiring first digital impression data for a first tooth within a patient's mouth (802). For example, a practitioner, such as a dentist, can use a dental scanning wand (e.g., the dental scanning wand 508 of FIG. 5) to capture digital image impression data for use in generating a digital impression for the tooth. In some implementations, the dental scanning wand is used to collect digital impression data for a tooth that is adjacent to a space where a tooth has been lost or is otherwise absent. In some implementations, the dental scanning wand is used to collect digital impression data for multiple teeth within a patient's mouth. For example, the dental scanning wand is used to collect digital impression data for teeth on either side of a space where a tooth has been lost or is otherwise absent. In some implementations, devices other than a dental scanning wand can be used to acquire the digital impression data. For example, Magnetic Resonance Imaging (MRI), fluoroscope or x-ray technology can be used to acquire the digital impression data. In some implementations, the digital impression data is acquired from the dental scanning wand (or other imaging device) by a computer system such as the computer system 510 of FIG. 5.

The process further includes acquiring second digital impression data for a gingival area extending between the first tooth and a second tooth within the patient's mouth. For example, the dental scanning wand (e.g., the dental scanning wand 508 of FIG. 5) can be used to gather digital impression data for a space extending between two teeth where a tooth has been lost or is otherwise absent. The acquired second digital impression data can include digital impression data for the second tooth, as well as digital impression data indicating a length of the space between the first tooth and the second tooth.

The process 800 further includes generating a three-dimensional model of a dental space maintainer using both the first and second digital impression data (806). The computer system can generate the CAD model such that the dental space maintainer defined by the CAD model is shaped to match contours of the first tooth for which digital impression data has been acquired so that a securing portion of the dental space maintainer can form a custom fit with the first tooth when the dental space maintainer is inserted into the patient's mouth. For example, the CAD model defines a shape for the inner surfaces of the securing portion of the dental space maintainer such that the inner surfaces of the securing portion conform to the contours of first tooth when the dental space maintainer is inserted into the patient's mouth. The computer system can also generate the CAD model such that the dental space maintainer defined by the CAD model includes a space maintaining portion that matches the length of the space between the first and second tooth. In some implementations, the CAD model defines portions of the outer surfaces of the dental space maintainer to engage teeth and gums in close proximity to the first tooth in a patient-specific, customized manner to define preferred embrasure forms and spacing between adjacent teeth.

The process 800 further includes transmitting data representing the three-dimensional model of the dental space maintainer to a rapid fabrication device (808). For example, the computer system can transmit data representing the three-dimensional model to a three-dimensional printer (e.g., the three-dimensional printer 114 of FIG. 1). The rapid fabrication device can use the transmitted data representing the three-dimensional model to create the dental space maintainer. After creation of the custom dental space maintainer, the dental space maintainer can be inserted into the patient's mouth to maintain proper spacing between the first and second teeth.

A number of embodiments of the invention have been described. Nevertheless, it will be understood that various modifications may be made without departing from the spirit and scope of the invention. Accordingly, other embodiments are within the scope of the following claims.

What is claimed is:

1. A system for providing a customized temporary dental crown, the system comprising:

a digital imaging dental tool configured to collect digital impression data for a first tooth positioned within a mouth of a patient;

a computer system configured to receive first digital impression data for the first tooth from the digital imaging wand, second digital impression data for the first tooth from the digital imaging wand, and third digital impression data for a gingival area extending between the first tooth and a second tooth, wherein the second digital impression data is collected by the digital imaging wand after portions of the first tooth have been removed, and wherein the computer system is further configured to generate a three-dimensional model of a temporary dental crown for the first tooth, the temporary dental crown including a space maintainer, wherein an outer portion of the temporary dental crown is at least partially defined to correspond to a first identified shape of the first tooth based at least partially on the first digital impression data and an inner portion of the temporary dental crown is at least partially defined to correspond to a second identified shape of the first tooth based at least partially on the second digital impression data, and wherein the space maintainer portion of the temporary dental crown is at least partially defined to correspond to a length of a space between the first tooth and the second tooth based at least partially on the third digital impression data;

a rapid fabrication device configured to receive data indicative of the three-dimensional model from the computer system and fabricate the temporary dental crown having the space maintainer according to the received data; and at least one temporary dental crown having a space maintainer, fabricated by the rapid fabrication device, the shape of the temporary dental crown being defined at least in part by the three-dimensional model generated by the computer system and corresponding to the first and second identified shapes of the first tooth, the space maintainer of the at least one temporary dental crown corresponding to the length of the space between the first tooth and the second tooth.

2. The system of claim 1, wherein the rapid fabrication device comprises a three-dimensional printer configured to create the temporary dental crown through deposition of multiple layers of fabrication material.

3. The system of claim 1, wherein internal surfaces of the temporary dental crown are shaped to conform to unique contours of the second identified shape of the first tooth to mate with the first tooth.

4. The system of claim 1, wherein the at least one temporary dental crown is fabricated from a semi-flexible material.

5. The system of claim 1 wherein the second digital impression data for the first tooth represents a prepared surface of the first tooth, wherein the prepared surface is created by removing portions of the first tooth and wherein the temporary dental crown includes an interior recess shaped to mate with the prepared surface of the first tooth.

6. The system of claim 5, wherein a shape of the temporary dental crown is at least partially defined based on a selected spatial relationship between the first tooth and the second tooth positioned adjacent to the first tooth, wherein the shape of the space maintainer portion of the temporary dental crown is at least partially defined to maintain proper spacing between the first tooth and the second tooth in the absence of a third tooth that had previously been positioned between the first tooth and the second tooth.

7. The system of claim 5, wherein the temporary dental crown is configured to receive the prepared surface of the targeted tooth within the interior recess, and wherein the temporary dental crown comprises solidified successive layers of a polymer material.

8. The system of claim 1, wherein the temporary dental crown further comprises exterior surfaces shaped to correspond to external contours of the first tooth that existed prior to the portions of the first tooth having been removed as exhibited by the second digital impression data.

9. The system of claim 1, wherein the space maintainer portion of the temporary dental crown is a loop space maintainer.

10. The system of claim 1, wherein the third digital impression data includes impression data for at least a portion of the second tooth and wherein at least part of the space maintainer of the at least one temporary dental crown corresponds to a shape of the second tooth based on the third digital impression data.

11. A method for using a temporary dental crown with a targeted tooth, the method comprising:

obtaining first digital impression data for a targeted tooth located within a patient's mouth prior to a tooth preparation procedure;

obtaining second digital impression data for a gingival area extending between the targeted tooth and an adjacent tooth prior to the tooth preparation procedure, wherein the gingival area extending between the targeted tooth and the adjacent tooth defines a space where a missing tooth had previously been present in the patient's mouth;

performing the tooth preparation procedure by preparing the targeted tooth of the patient in a dental facility building for receiving a temporary dental crown;

obtaining third digital impression data for the targeted tooth after the tooth preparation procedure;

after obtaining the third impression data for the targeted tooth, fabricating at a rapid fabrication device in the dental facility building a patient-specific temporary dental crown for insertion over the targeted tooth of the patient, the patient-specific temporary dental crown being fabricated based at least in part on the first, second, and third digital impression data for the targeted tooth of the patient, the temporary dental crown including a space maintainer that is at least partially defined to correspond to a dimension of the space between the targeted tooth and the adjacent tooth; and affixing the patient-specific temporary dental crown to the targeted tooth of the patient in the dental facility building, such that the space maintainer portion of the temporary dental crown contacts the adjacent tooth.

12. The method of claim 11, further comprising, prior to fabricating the patient-specific temporary dental crown, obtaining fourth digital impression data for one or more teeth opposing the targeted tooth; wherein the patient-specific temporary dental crown is fabricated based at least in part on the fourth digital impression data for the one or more teeth opposing the targeted tooth.

13. The method of claim 11, wherein the rapid fabrication device fabricates the patient-specific temporary dental crown by depositing sequential layers of a polymer material.

14. The method of claim 11, wherein the space maintainer portion of the temporary dental crown is a loop space maintainer.

15. The method of claim 11, wherein the second digital impression data includes impression data for at least a portion of the adjacent tooth and wherein at least part of the space maintainer portion of the temporary dental crown corresponds to a shape of the adjacent tooth based on the second digital impression data.

16. The method of claim 11, wherein the space maintainer portion of the temporary dental crown comprises a bilateral space maintainer.

17. A method for creating a customized temporary dental crown, the method comprising:

acquiring, by a computer system, first digital impression data for external contours of a targeted tooth positioned within a mouth of a patient;

acquiring, by the computer system, second digital impression data for a gingival area extending between the targeted tooth and an adjacent tooth, wherein the gingival area extending between the targeted tooth and the adjacent tooth defines a space where a missing tooth had previously been present in the patient's mouth;

acquiring, by the computer system, third digital impression data for a prepared surface of the targeted tooth defined by removal of the external contours of the targeted tooth;

generating, by the computer system, a three-dimensional model of a temporary dental crown for insertion over the first tooth, wherein an exterior shape of the temporary dental crown is defined to correspond to the targeted tooth based at least partially on the first digital impression data, an interior shape of the temporary dental crown is defined to correspond to the prepared surface of the targeted tooth based at least partially on the third digital impression data, and a space maintainer portion of the temporary dental crown is defined to correspond to a dimension of the space between the targeted tooth and the adjacent tooth based at least partially on the second digital impression data; and transmitting, by the computer system, data representing the three-dimensional model to a rapid fabrication device for fabricating the temporary dental crown shaped to mate with the targeted tooth.

18. The method of claim 17, further comprising:

fabricating, by the rapid fabrication device, the temporary dental crown defined by the three-dimensional model, wherein the fabrication occurs while the patient is present in a dental facility in which the rapid fabrication device is also located.

19. The method of claim 17, wherein:

the first and second digital impression data for the targeted tooth and space between the targeted tooth and the adjacent tooth is acquired by the computer system prior to a tooth preparation procedure for the targeted tooth; and;

the third digital impression data for the targeted tooth is acquired by the computer system after the tooth preparation procedure for the targeted tooth.

20. The method of claim 17, wherein the second digital impression data includes impression data for at least a portion of the adjacent tooth and wherein at least part of the space maintainer portion of the temporary dental crown corresponds to a shape of the adjacent tooth based on the second digital impression data.

* * * * *